(12) United States Patent
Friedman et al.

(10) Patent No.: US 7,074,192 B2
(45) Date of Patent: Jul. 11, 2006

(54) METHOD AND APPARATUS FOR MEASURING BLOOD PRESSURE USING RELAXED MATCHING CRITERIA

(75) Inventors: Bruce Arnold Friedman, Tampa, FL (US); Richard Medero, Tampa, FL (US); Lawrence T. Hersh, Tampa, FL (US); Sai Kolluri, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 466 days.

(21) Appl. No.: 10/613,333

(22) Filed: Jul. 3, 2003

(65) Prior Publication Data
US 2005/0004477 A1    Jan. 6, 2005

(51) Int. Cl.
*A61B 5/02* (2006.01)
(52) U.S. Cl. ..................................... 600/494
(58) Field of Classification Search ................ 600/493, 600/494, 495
See application file for complete search history.

(56) References Cited

U.S. PATENT DOCUMENTS

| | | | |
|---|---|---|---|
| 4,543,962 A | 10/1985 | Medero et al. | 128/682 |
| 4,638,810 A | 1/1987 | Ramsey, III et al. | 128/681 |
| 4,796,184 A | 1/1989 | Bahr et al. | 364/413.03 |
| 4,889,133 A | 12/1989 | Nelson et al. | 128/681 |
| 4,949,710 A | 8/1990 | Dorsett et al. | 128/680 |
| 5,579,776 A | 12/1996 | Medero | 128/680 |
| 5,704,362 A | 1/1998 | Hersh et al. | 128/680 |
| 6,358,213 B1 | 3/2002 | Friedman et al. | 600/493 |
| 6,423,010 B1* | 7/2002 | Friedman et al. | 600/494 |
| 6,440,080 B1 | 8/2002 | Booth et al. | 600/494 |
| 6,485,429 B1 | 11/2002 | Forstner | 600/494 |
| 2002/0082507 A1 | 6/2002 | Kolluri et al. | 600/485 |
| 2002/0143259 A1 | 10/2002 | Stergiopoulos et al. | 600/490 |

FOREIGN PATENT DOCUMENTS

| | | |
|---|---|---|
| GB | 2336407 A | 10/1999 |
| JP | 2000339393 A | 2/2000 |

OTHER PUBLICATIONS

Nelson, Robert M. et al., Determination of accuracy in neonates for non-invasive blood pressure device using an improved algorithm, Blood Pressure Monitoring 2002, vol. 7 No. 2, pp. 123-129, Received: May 24, 2001 Revised: Oct. 29, 2001 Accepted: Nov. 13, 2001.

(Continued)

*Primary Examiner*—Robert L. Nasser
*Assistant Examiner*—Vikram P. Sundararaman
(74) *Attorney, Agent, or Firm*—Fletcher Yoder

(57) ABSTRACT

A technique for comparing pressure oscillations obtained during a blood pressure determination wherein two or more sets of matching criteria may be employed. The set of matching criteria to be employed is determined based on the heart rate variability or the presence of heart beat irregularities or arrhythmias as determined by an independent heart monitor, such as an ECG. The selected set of matching criteria may then be employed in determining the acceptability of the time interval between two oscillations and the equivalence of the two oscillations based upon one or more oscillation characteristics, such as peak amplitude. In this manner, non-consecutive oscillations may be matched and used in determining blood pressure.

20 Claims, 6 Drawing Sheets

OTHER PUBLICATIONS

Ramsey, Maynard III, Knowing your Monitoring Equipment, Blood Pressure Monitoring: Automated Oscillometric Devices, Journal of Clinical Monitoring, vol. 7 No. 1, pp. 57-67, Received: Oct. 17, 1989 Revised: Feb. 12, 1990 Accepted: Jun. 19, 1990.

* cited by examiner

METHOD AND APPARATUS FOR MEASURING BLOOD PRESSURE USING RELAXED MATCHING CRITERIA

BACKGROUND OF THE INVENTION

The present technique relates generally to monitoring blood pressure using an oscillometric technique. More specifically, the present technique relates to improving the performance of an oscillometric blood pressure estimation in the presence of arrhythmias, such as premature ventricular complexes (PVC's).

The oscillometric method of measuring blood pressure typically involves applying an inflatable cuff around an extremity of a patient's body, such as the patient's upper arm. The cuff is then inflated to a pressure above the patient's systolic pressure and then incrementally reduced in a series of small steps. A pressure sensor measures the cuff pressure at each step. The sensitivity of the sensor is such that pressure fluctuations within the artery resulting from the beating of the patient's heart may be detected. In particular, the pulses are transferred to the inflated cuff causing slight pressure variations within the cuff, which are detected by the pressure sensor in the monitor. The pressure sensor produces an electrical signal based on the measured cuff pressure. The electrical signal comprises a DC component, representing the constant cuff pressure at the pressure step, and a series of small periodic components, representing the pressure variations attributable to the beating of the patient's heart. These small periodic components are often referred to as "oscillation complexes" or simply "oscillations".

A patient's blood pressure may be estimated based on an analysis of these oscillation complexes. After filtering out the DC component and amplifying the signal generated by the cuff pressure sensor, peaks may be determined for each oscillometric complex. At each decreasing pressure step, the peaks will tend to increase until a maximum amplitude is reached. Once this maximum amplitude has been reached, the peaks will begin to decrease with each decreasing pressure step. This maximum amplitude has been found to be representative of the patient's mean arterial pressure. The systolic and/or diastolic pressures can be derived either as the cuff pressures at which the oscillation amplitude is a predetermined fraction of the maximum amplitude, or by estimation techniques using direct processing of the oscillation complexes.

To improve accuracy and allow artifact rejection consecutive peak matching has been employed. Using this peak matching technique, oscillometric complexes at a given pressure step must have amplitude and pulse period characteristics that match within predetermined thresholds. Failure of two complexes to match may result in additional measurements being taken at the pressure step until two or more consecutive peaks are obtained which do match. In the presence of arrhythmias, such as PVC's, or noise, consecutive peak matching can prolong or prevent blood pressure determination, depending on the length of time needed to obtain consecutive matching peaks. Matching of non-consecutive peaks may also be employed but may be complicated by the difficulties associated with matching pulse periods. In addition, PVC's and other arrhythmias alter peak amplitudes in addition to pulse periods, further complicating the process of obtaining matches. Therefore, a need exists for a technique allowing the rapid and accurate measurement of blood pressure in a non-invasive manner in the presence of arrhythmias, such as PVC's.

BRIEF DESCRIPTION OF THE INVENTION

The present technique relates to the measurement and comparison of oscillation complexes during the non-invasive determination of blood pressure. In particular, the present technique provides for the use of an independent source of information concerning heart rate, heart rate variability, or arrhythmias. The heart rate variability and arrhythmia information thereby obtained may be used to select a suitable set of matching criteria. For example, different matching criteria, some of which are relaxed compared to their use in normal circumstances, may be selected when heart rate variability exceeds some threshold or when arrhythmias are indicated. Using the selected set of criteria, oscillations at a given pressure step are compared to determine if the intervening time interval is consistent with the independently measured heart rate. The oscillations at the pressure step are also compared, using the selected set of criteria, to determine if the oscillations are substantially equivalent in view of one or more oscillation characteristics, such as peak amplitude. In this manner, non-consecutive oscillations may be compared and utilized in the determination of blood pressure.

In one embodiment of the present technique, a method is provided for comparing oscillations during a blood pressure determination. The method comprises acquiring at a pressure increment a first and second oscillation having one or more oscillation characteristics. A corresponding reference time interval between the first oscillation and the second oscillation is acquired via an independent heart rate monitoring device and a set of matching criteria is selected based upon the additional heart monitor signal. Whether the time interval between oscillations is substantially an integer multiple of a reference time interval is determined. In addition, it is determined whether the first oscillation and the second oscillation are substantially equivalent based upon the respective one or more oscillation characteristics and upon the selected set of matching criteria.

In another embodiment of the present technique, a tangible medium for comparing oscillations during a blood pressure determination is provided. The tangible medium comprises routines for acquiring at a pressure increment a first and a second oscillation having one or more oscillation characteristics. The tangible medium also comprises a routine for acquiring a time interval between the first oscillation and the second oscillation via a heart monitor signal generated by an independent heart rate monitoring device. Routines for selecting a set of matching criteria based upon the heart monitor signal and for determining whether the time interval is substantially an integer multiple of a reference time interval are also included. In addition, a routine for determining whether the first oscillation and the second oscillation are substantially equivalent based upon the respective one or more oscillation characteristics and upon the selected set of matching criteria may also be present.

In a further embodiment of the present technique, a non-invasive blood pressure monitor is provided. The non-invasive blood pressure monitor comprises means for acquiring a first and a second oscillation at a pressure increment and means for independently acquiring a time interval between the first and second oscillations. The monitor also comprises means for selecting a set of matching criteria and means for determining whether the time interval is substantially an integer multiple of a reference time interval. In addition, means for determining whether the first oscillation and the second oscillation are substantially equivalent based upon the selected set of matching criteria is also present.

In an additional embodiment of the present technique, a non-invasive blood pressure monitor is provided. The monitor comprises a pressure cuff configured to be pressurized by a source of pressurized air via an inflate valve and configured to be deflated via a deflate valve. In addition, a pressure transducer configured to determine the pressure within the pressure cuff and to generate a pressure signal and a heart monitoring device configured to generate a heart rate signal are present in the monitor. The monitor also includes a processing unit configured to receive the pressure signal and the independent heart rate signal. The processing unit is configured to acquire two or more oscillations at a pressure increment from the pressure signal and to determine a time interval separating two oscillations from the heart monitor signal. The processing unit is further configured to select a set of matching criteria based upon the heart rate signal and to determine whether the time interval is substantially an integer multiple of a reference time interval determined from the heart rate monitor. Further, the processing unit is configured to determine whether the two oscillations are substantially equivalent based upon the selected set of matching criteria.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
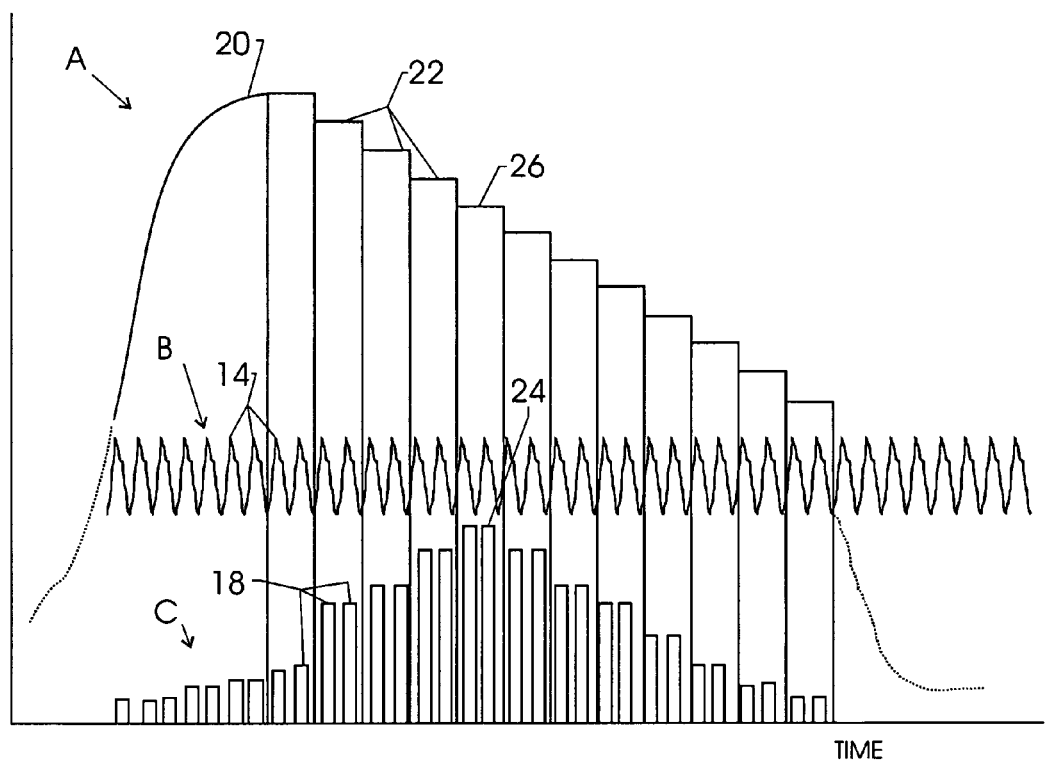
FIG. 1 is a diagram showing various waveforms associated with an oscillometric blood pressure measurement.

The present technique relates to the non-invasive determination of blood pressure, particularly in the presence of arrhythmias. In particular, the technique provides for the rapid and accurate determination of blood pressure using oscillometric techniques. An example of the use of these oscillometric techniques, absent arrhythmias or noise, is depicted in FIG. 1. In FIG. 1, various waveforms are depicted, including a cuff pressure waveform, depicted by reference letter A, which represents the overall pressure of the inflatable cuff at any given time. Also depicted in FIG. 1, is the arterial pressure waveform, depicted by reference letter B, represented as a series of blood pressure pulses 14, which represents the periodic blood pressure variations corresponding to a patient's pulse. A pressure oscillation curve, depicted by reference letter C in FIG. 1, is also present and comprises a series of cuff pressure oscillation complexes 18, each of which is associated with a respective blood pressure pulse 14. The cuff pressure oscillation complexes 18 may vary in amplitude based upon the characteristics of the respective blood pressure pulse 14 and cuff pressure. The various waveforms depicted in FIG. 1 are provided to assist in visualizing one or more concepts discussed herein and are not, therefore, presented to scale with respect to one another.

As can be seen from waveform A, the cuff pressure is first inflated to a maximum pressure 20, and then reduced in a series of incremental steps 22. Blood pressure pulses 14 are measured at each incremental cuff pressure 22. The amplitudes of the associated oscillation complexes 18 increase with each decrement of cuff pressure 22 until a maximum amplitude 24 is reached at corresponding cuff pressure 26. The amplitudes of the oscillation complexes 18 diminish with subsequent reductions in cuff pressure 22. Thus, the cuff pressure 26 corresponding to the oscillation complex 18 with the maximum amplitude 24 represents the patient's mean arterial pressure, and the patient's systolic and diastolic pressures may be determined therefrom.

Unfortunately, blood pressure measurements based on measurements of this type may be skewed due to artifacts caused by patient motion or by arrhythmias. Events such as these can adversely affect the amplitudes of the oscillation complexes 18 detected by the cuff's pressure sensor, resulting in erroneous blood pressure measurements. Consequently, selected parameters, such as amplitude or period, of consecutive oscillation complexes 18, may be measured and evaluated in view of various matching criteria to allow aberrant data to be identified and/or eliminated. Therefore, at least two oscillation complexes 18 are typically measured at each cuff pressure 22 before the cuff pressure 22 is decremented, as shown in FIG. 1.

Because, the duration of the blood pressure determination procedure is related to the number of oscillation complexes 18 measured, i.e., fewer measurements result in a shorter determination duration, it is generally desirable to minimize the number of oscillation measurements, such as to two per pressure step 22. However, in the presence of an arrhythmia, the number of oscillometric complexes 18 measured at one or more of the pressure steps 22 may increase. In particular, consecutive oscillations 18 may not match, resulting in additional complexes 18 being measured until the matching criteria is satisfied, a timeout occurs for that pressure step 22, or a timeout occurs for the determination process as a whole.

Figure 2:
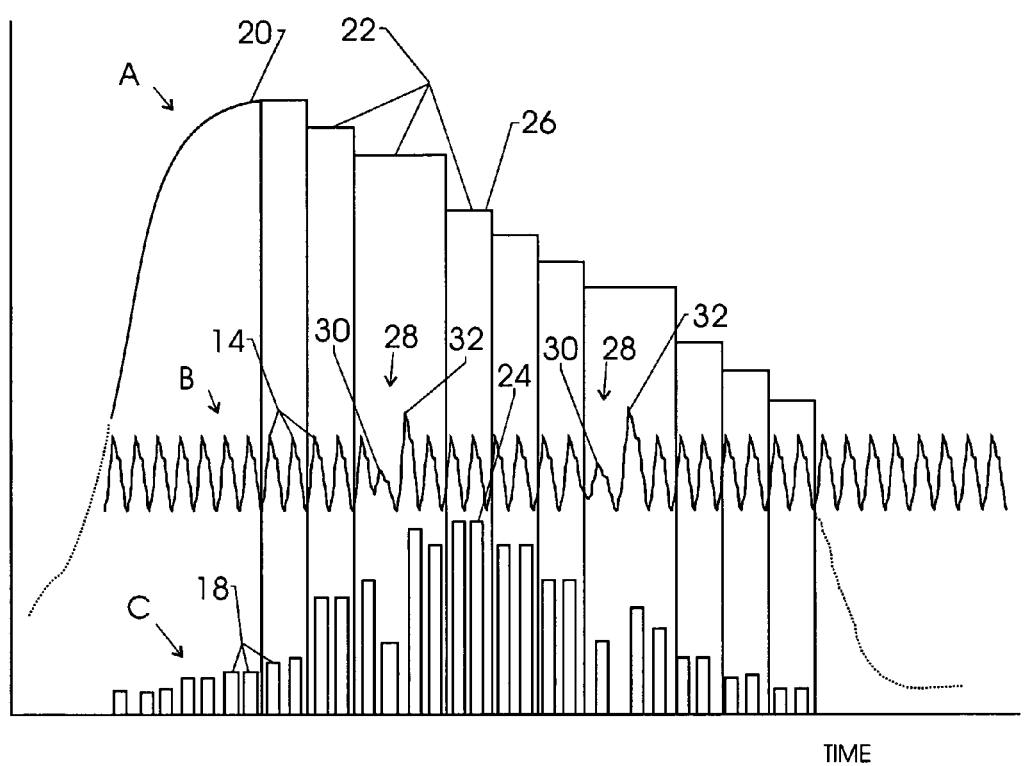
FIG. 2 is a diagram showing various waveforms associated with an oscillometric blood pressure measurement where arrhythmias are present.

For example, as depicted in FIG. 2, premature ventricular complexes (PVC's) 28 may be present which affect both the amplitude and the period of the PVC blood pressure pulse 30 as well as the subsequent blood pressure pulse 32. In particular, because the heartbeats associated with the PVC occurs prematurely, a smaller amount of blood is pumped from the heart than would otherwise be the case and the arterial pressure associated with the PVC 28 is reduced. As can be seen in FIG. 2, the amplitude of oscillation complex 18 associated with the PVC 30 is similarly reduced. Likewise, because the time between the PVC 28 and the subsequent beat is extended, the subsequent beat pumps a greater amount of blood than normal and the amplitude of the subsequent pressure pulse 32 and the associated complex 18 is therefore increased.

Because of these variations in period and amplitude between the oscillation complexes 18 associated with an arrhythmia, such as PVC 28, the oscillation complexes 18 will not match with one another or with adjacent complexes 18 if the matching criteria are too conservative. Additional measurements may therefore be performed until consecutive matching oscillation complexes 18 are observed at the pressure step 22 or until a timeout occurs for the step 22 or for the entire determination.

Figure 3:
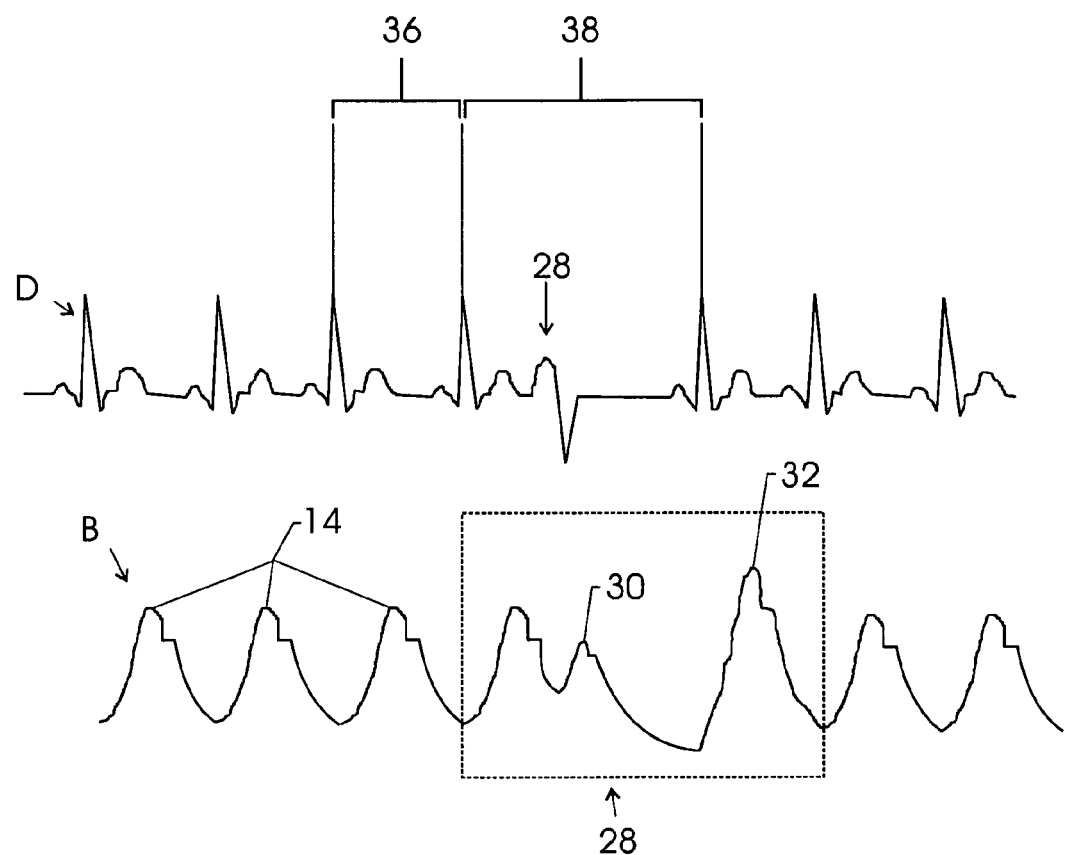
FIG. 3 is a diagram showing an ECG waveform containing arrhythmias and a respective blood pressure waveform.

Corresponding electrocardiogram (ECG) data, depicted as waveform D in FIG. 3, may be useful for determining the occurrence of a PVC 28 or other arrhythmia and may be particularly useful for determining the timing of such events. When seen in conjunction with the corresponding arterial pressure waveform, i.e., waveform B, the ECG data points can be seen to correspond with respective points on the arterial pressure waveform. The ECG waveform can therefore be useful in determining the presence of arrhythmias and may assist in determining whether matching criteria are met, particularly in regard to the pulse period. For example, a standard pulse period 36 can be seen in the ECG waveform, depicted as waveform D, prior to the PVC 28 while an extended pulse period 38 can be seen spanning normal beats with an intervening PVC 28. Thus, the simultaneously acquired ECG waveform may provide useful information in conjunction with the arterial pressure waveform in identifying and removing aberrant beat information, such as PVC 28. Similarly, though the ECG data is discussed in this context, other physiological indicators may also be independently acquired and used to identify and remove aberrant beats from the arterial pressure waveform, depicted by waveform B. For example, photoplethysmographs, accelerometers, impedance plethysmographs or acoustic measurement devices may provide similar independent information.

Figure 4:
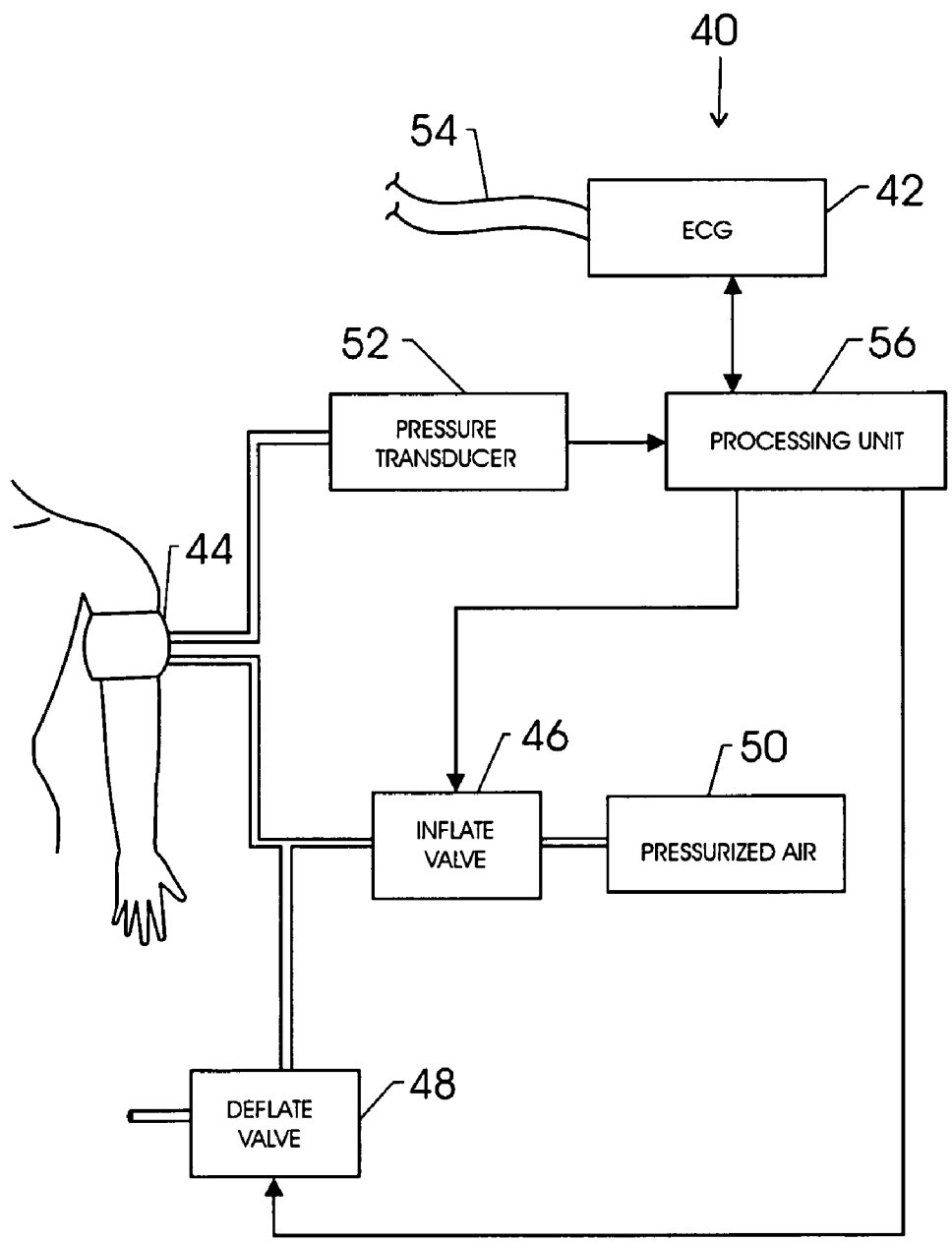
FIG. 4 is a functional block diagram of a blood pressure monitor according to one embodiment of the present technique.

An example of a non-invasive blood pressure monitoring system 40 utilizing an independent information source, such as an ECG 42, is depicted in FIG. 4 in a functional block diagram. The non-invasive blood pressure monitoring system 40 includes an inflatable cuff 44 adapted to be inflated around a portion of a patient's body, such as around the patient's arm. An inflate valve 46 and a deflate valve 48 are operatively connected to the cuff 44 to control the air pressure within the cuff 44. The inflate valve 46 regulates air flow between the cuff 44 and a source of pressurized air 50. Similarly, the deflate valve 48 regulates air flow between the cuff 44 and the atmosphere. A pressure transducer 52 is provided which measures pressure within the interior of the cuff 44. The ECG 42 may be provided with leads 54 connected to electrodes attached to the patient's body. A processing unit 56 is also provided to control the air pressure within the cuff 44 and to receive and interpret pressure and heart rate data from the pressure transducer 52 and the ECG monitor 42 respectively. The processing unit 56 may execute routines stored locally, such as on a local hard drive, optical drive, or memory device, or remotely, such as on a network accessible location or server, to perform various functions.

In operation, input from the pressure transducer 52 is received and analyzed by the processing unit 56 which controls the inflate valve 46 and deflate valve 48 to maintain a desired pressure within the inflatable cuff 44. In accordance with the oscillometric method of measuring blood pressure, upon initiation of a blood pressure measurement the deflate valve 48 is closed and the inflate valve 46 is opened, thereby pressurizing the cuff 44 with pressurized air from source 50. Routines executed by the processing unit 56 monitors the output from the pressure transducer 52 and close the inflate valve 46 when the pressure within the cuff 44 exceeds the patient's systolic blood pressure. Thereafter, routines executed by the processing unit 56 reduce the cuff pressure in a series of incremental steps 22 by selectively opening and closing the deflate valve 48, thereby venting pressurized air within the cuff 44 to atmosphere.

In addition to sensing the overall cuff pressure, the pressure transducer 52 senses oscillometric complexes 18 superimposed on the overall cuff pressure signal. In particular, the signal from pressure transducer 52 comprises a DC component, representing the static pressure of the inflated cuff 44 at the particular pressure increment at which the measurement is taken, plus a variable component, the oscillation complexes 18, resulting from variations in the cuff pressure caused by the patient's pulse. The pressure transducer signal is received by the processing unit 56 where routines executed by the processing unit 56 isolate, amplify and process oscillation complexes 18 from the constant DC signal.

The oscillometric complexes 18 may then be analyzed by other routines executed by the processing unit 56 to determine the characteristics of the oscillation complexes 18. Once the various characteristics of the oscillation complexes 18 have been determined, routines executed by the processing unit 56 may compare the measured characteristics, using one or more matching criteria, to determine if two or more consecutive oscillometric complexes 18 are substantially equivalent at a given pressure step 22. Based upon this analysis, the routines governing the process may decrement the cuff pressure to the next pressure step 22 or may stop the determination process due to successful completion or due to an error condition such as a timeout. Upon successful completion of the process, the patient's mean arterial pressure (MAP) may be calculated using the measured characteristics, such as the maximum peak amplitude 24 of the oscillometric complexes 18. The systolic and diastolic pressures may be calculated from the MAP by determining the cuff pressure at which the oscillation complexes 18 are fractions of the maximum amplitude 24. They may also be determined by evaluating changes in the rate of increase or decrease in the amplitudes of the oscillation complexes 18.

Figure 5:
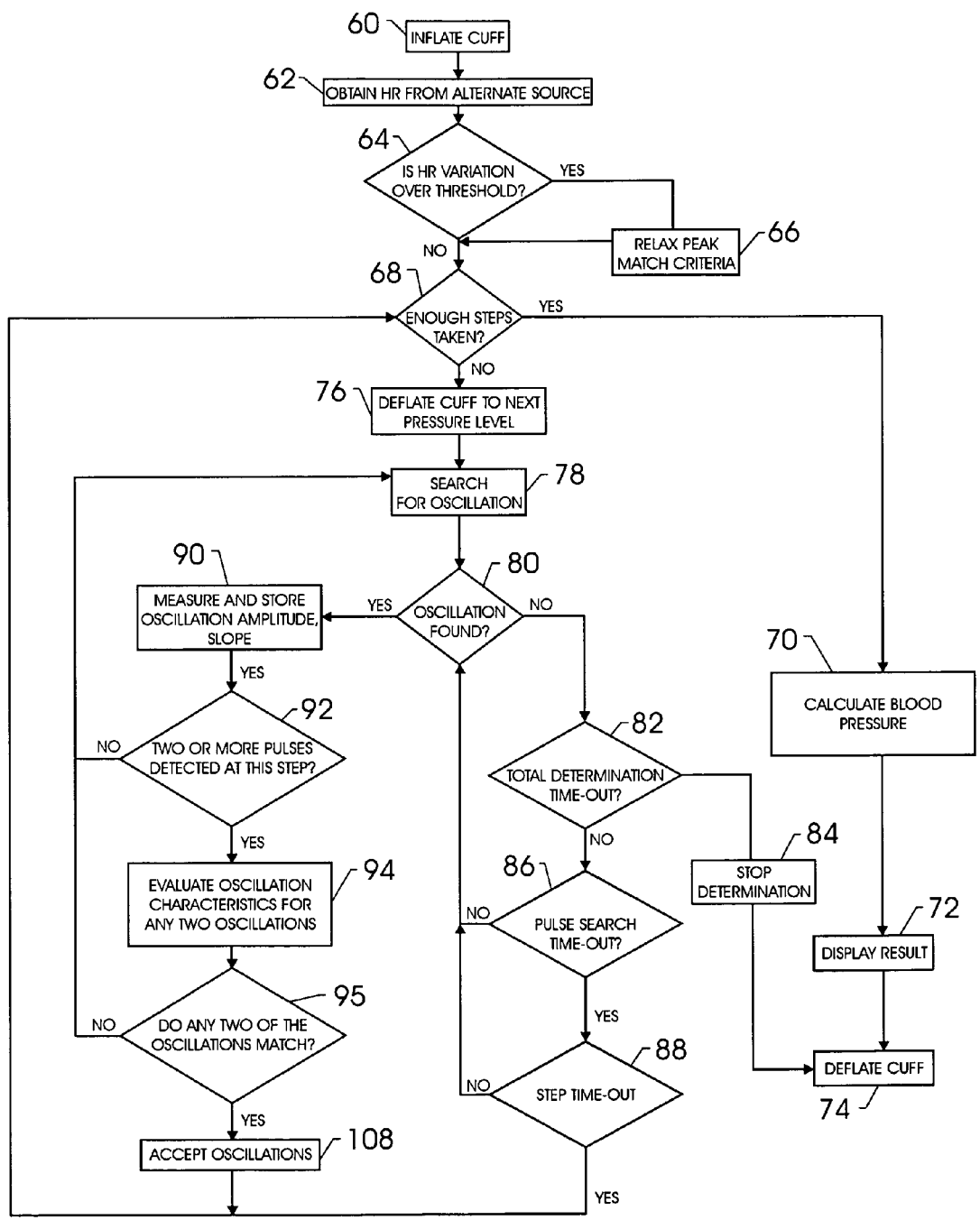
FIG. 5 is a flow chart describing one embodiment for measuring blood pressure according to the present technique.

As noted above, comparisons are made between consecutive oscillometric complexes 18 at each pressure increment 22 to determine the sufficiency of data at that increment 22. The present technique may aid in the matching of oscillometric complexes 18 and is discussed in greater detail in FIGS. 5 and 6. Referring first to FIG. 5, the pressure cuff 44 is positioned on the patient and inflated to the maximum pressure 20, as depicted at step 60. The patient's heart rate may then be determined from a separate source, such as ECG 42, as depicted at step 62. The variation of the heart rate, as determined by routines running on the processing unit 56, may then be compared to a threshold value at decision block 64. The threshold value may be either predetermined or selected by an operator.

If the heart rate variation exceeds the threshold value, the matching criteria to be employed in comparing consecutive oscillation complexes 18 may be relaxed at step 66. Alternately, the matching criteria may be relaxed at step 66 based upon the presence of certain arrhythmias, such as a trial fibrillations, which may be detected by the independent heart monitor, such as ECG 42. The matching criteria selected may then be used in the subsequent processing and comparison of oscillation complexes 18. For example, a measurement and comparison routine using an unrelaxed matching criteria might find two oscillation complexes 18 substantially equivalent if the difference in their respective peak amplitudes is less than 10%. However, if the heart rate variability indicates the presence of arrhythmias or PVC's, a relaxed criteria of 20% allowable difference may be employed. Use of the relaxed criteria when amplitude variability is deemed more likely may allow the complexes 18 being compared to be classified as substantially equivalent, i.e., matching, despite greater amplitude variability than would otherwise be acceptable.

After selection of the appropriate matching criteria, the processing unit 56 evaluates whether enough deflation steps have occurred 68 based on an operator selected or predetermined threshold or upon the sufficiency of the acquired data. If the processing unit 56 determines that enough deflation steps have been taken at decision block 68, the blood pressure, such as the mean arterial pressure, may be calculated at step 70 and displayed at step 72. After blood pressure determination, the cuff 44 may be completely deflated, as depicted at step 74.

However, if additional steps are required, the cuff 44 is deflated to the next pressure increment 22 at step 76. After the cuff 44 has been deflated to the next pressure increment 22, the processing unit 56 searches for a pressure oscillation 18 at step 78 and a determination of whether an oscillation 18 is detected by the pressure transducer 52 is made at decision block 80. For example, a concurrent algorithm may be initiated at step 78 which looks for an oscillation. When this concurrent algorithm ends it returns one of two conditions: an oscillation has been found or the time allotted for searching for an oscillation has elapsed. These conditions are used by the main loop consisting of steps 80, 82, and 86 to control the progression of the processing needed at each step. If the concurrent oscillation detection algorithm does find an oscillation it may provide an array of sample values for use in step 90.

If no oscillations 18 are detected, the processing unit 56 determines whether the total determination time has been exceeded at decision block 82. If the determination time has been exceeded, the determination process may be stopped, at step 84, and the cuff deflated at step 74. If the determination time is not exceeded, the processing unit 56 may determine whether the pulse search time has been exceeded at decision block 86. If neither the determination time nor the pulse search time has been exceeded, the processing unit 56 again determines whether an oscillation 18 has been found at decision block 80. The steps of determining whether an oscillation has been located or whether the determination or pulse search times have been exceeded, i.e., steps 80, 82, and 86, may constitute a processing loop of a program that runs each time a sample is taken, and which is exited when the algorithm finds an oscillation 18 or when the processing unit 56 has determines that a timeout has occurred.

If the pulse search time is exceeded, as determined at decision block 86, the processing unit 56 determines if a step time out has occurred at decision block 88. If the step time has not been exceeded, the processing unit 56 returns to the processing loop discussed above and determines whether an oscillation 18 has been found at decision block 80. If a step time is determined to have occurred at block 88, the processing unit 56 may return to decision block 68 to determine is sufficient steps have been taken and the cuff 44 is deflated to the next increment 22 at step 76 if more deflation steps are required.

If an oscillation 18 is detected at decision block 80, however, routines may be executed by the processing unit 56 at step 90 to measure the amplitude and slope of the oscillation 18. At decision block 92, the processing unit 56 determines whether two or more oscillation pulses 18 have been detected. If only one oscillation 18 has been detected, a search is made for additional oscillations 18 at step 78. If two or more oscillations 18 have been detected, the processing unit 56 may evaluate various parameters of the oscillations 18 at step 94. For example, the processing unit 56 may evaluate the pulse period, the time to peak of the oscillations 18, the slope of the oscillations 18, and the amplitude of the oscillations 18.

Figure 6:
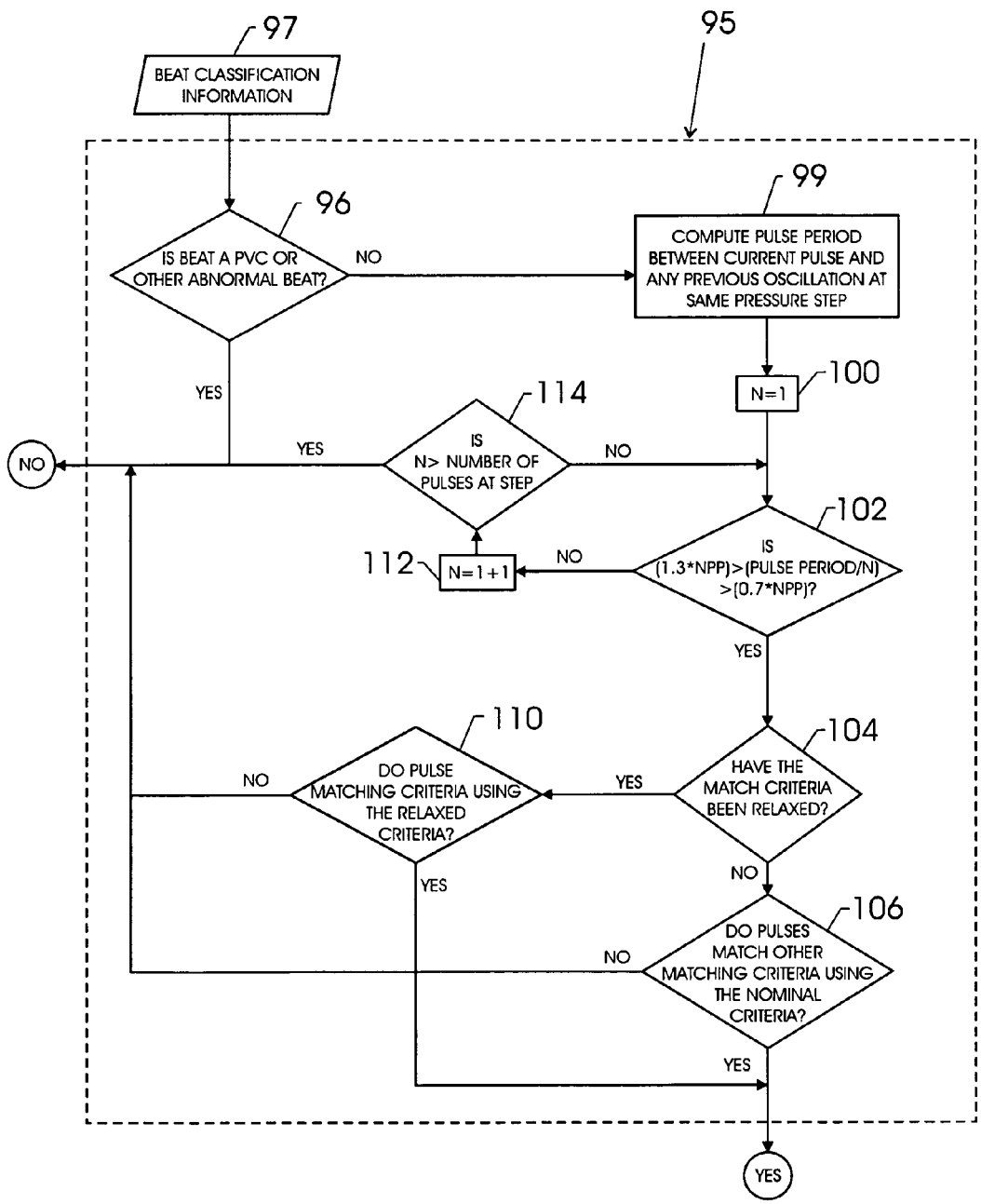
FIG. 6 is a flow chart describing one embodiment of a technique for determining whether pressure oscillations satisfy a selected matching criteria.

A determination may be made at decision block 95, based on the evaluated parameters, whether the selected matching criteria are satisfied by the oscillations 18. The matching determination of decision block 95 is depicted in detail in the outlined box of FIG. 6. Referring now to FIG. 6, an initial determination may be made whether one of the respective oscillations 18 is associated with a PVC or an abnormal beat at decision block 96. If available, beat classification information 97 may be obtained to facilitate this determination. For example, the beat classification information 97 may be obtained from an ECG 42 or from the source of the heart rate information obtained at step 62. If an oscillation 18 is associated with a PVC or an abnormal beat, a determination is made that the oscillation 18 does not match and the matching routine in block 95 is exited. The processing unit 56 returns to searching for another oscillation 18 at step 78, as depicted in FIG. 5.

Referring once again to FIG. 6, if the beat associated with the oscillation 18 is not determined to be abnormal at decision block 96, the processing unit 56 computes a time interval, i.e., a pulse period, between like points of the current and previous oscillations 18, as depicted at step 99. The points on the oscillations 18 serving as the basis for the pulse period may be peaks or major inflection points known to be present in the arterial pressure waveform, depicted as waveform B. The processing unit 56 then determines whether the current pulse period is a multiple of a reference time interval. For example, at step 100, the processing unit 56 may set a counter, N, to 1. The processing unit 56 may then determine whether the current pulse period divided by N is within a specified range, as depicted at decision block 102. For example, the high value for the range may be calculated by multiplying a reference time interval by a factor, such as 1.3, while the low value may be calculated by multiplying the time interval by a different factor, such as 0.7. The factors, of course, may be varied to produce the desired range. For instance, if the matching criteria were relaxed at step 66 the high and low threshold values may be adjusted to allow for greater deviation of the pulse period from the reference time interval.

The reference time interval may be a set or a calculated time interval. In one embodiment, the reference time interval is an average time interval, i.e., an average pulse or heartbeat interval, determined from the patient. Other statistical measures of central tendency may also be employed. The measurements constituting the basis for the reference time interval may be performed by an independent apparatus, such as ECG 42, before or during the procedure. In another embodiment, the reference time interval is derived from measurements made by the pressure transducer 52 and the processing unit 56 at previous pressure increments 22.

If, as determined at decision block 102, the current pulse period divided by N is within the time interval range, i.e., the pulse occurred when expected, the processing unit 56 determines whether the match criteria have been relaxed at step 104. If not, the processing unit 56 determines whether any remaining match criteria are met for the current oscillation 18 at block 106. If these criteria are met, the processing unit 56 exits the matching routine of decision block 95 and accepts the oscillations 18 at step 108. If the remaining match criteria are not met, the processing unit 56 exits the matching routine of block 95 and returns to searching for oscillations at step 78 unless the step time limit has been exceeded, as determined at decision block 97.

Similarly, if the match criteria were relaxed, the processing unit 56 evaluates whether any remaining match criteria are met for the current oscillation 18 using the relaxed criteria at step 110. If the relaxed match criteria are met, the processing unit 56 accepts the oscillations 18 at step 108. If the relaxed match criteria are not met, the processing unit 56 returns to searching for oscillations at step 78. Examples of oscillation parameters which may be evaluated based on the matching criteria at steps 106 and 110 include oscillation amplitude and slope variations relative to their nominal or expected values. Time-to-peak interval, i.e., the time from the beginning of the oscillation to its maximum may also be evaluated under the respective matching criteria of steps 106 and 110.

If, however, the current pulse period divided by N is not within the specified time interval range, as determined at decision block 102, N is incremented by 1 at step 112. A determination is then made whether the value of N exceeds the number of oscillations 18 at the pressure step 22 at step 114. If N exceeds the number of oscillations 14 at the pressure step 22, the current pulse period is not an integer multiple of the reference time period and the processing unit 56 may exit the matching routine and return to searching for oscillations at step 78. If N is less than or equal to the number of oscillations 18 at the pressure increment 22, the processing unit 56 determines whether the pulse period divided by the incremented value of N is within the specified range at step 102. In this manner, non-adjacent oscillations 18 may be selected for further review under the remaining matching criteria. Once a pulse period divided by a value of N is determined to be within the specified range at step 102, a determination is made whether the remaining matching criteria are met for the oscillations 18 at step 106 or 110, depending on whether the matching criteria were unrelaxed or relaxed, respectively.

Referring once again to FIG. 5, if the oscillations 18 are determined to be matched by the matching routine of decision block 95, the oscillations 18 are accepted at step 108. The processing unit 56 may then make a determination of whether the blood pressure determination is complete at step 68. If the determination process is complete, the processing unit 56 calculates the blood pressure at step 70 and the blood pressure may be displayed, as indicated at step 72. If, however, the processing unit 56 determines that the operation is not complete, the cuff 44 is deflated to the next pressure increment 22 and the operation is continued until the determination is completed or a timeout occurs.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for comparing oscillations during a blood pressure determination, comprising:
   acquiring at a pressure increment a first oscillation having one or more oscillation characteristics;
   acquiring at the pressure increment a second oscillation having the one or more oscillation characteristics;
   acquiring a time interval between the first oscillation and the second oscillation via a heart monitor signal generated by an independent heart rate monitoring device;
   selecting a set of matching criteria based upon the heart monitor signal;
   determining whether the time interval is substantially an integer multiple of a reference time interval using the selected set of matching criteria; and
   determining whether the first oscillation and the second oscillation are substantially equivalent based upon the respective one or more oscillation characteristics and upon the selected set of matching criteria.

2. The method as recited in claim 1, wherein the one or more oscillation characteristics comprise a peak amplitude.

3. The method as recited in claim 1, wherein the independent heart rate monitoring device is at least one of an electrocardiograph, a photoplethysmograph, an accelerometer, an impedance plethysmograph, and an acoustic heart monitor.

4. The method as recited in claim 1 wherein the heart monitor signal is an electrocardiogram.

5. The method as recited in claim 1, wherein the heart monitor signal comprises at least one of a heart rate, a measure of heart rate variability, and an indicator of the presence of arrhythmias.

6. The method as recited in claim 1, wherein selecting a set of matching criteria comprises selecting one of a set relaxed matching criteria and a set of unrelaxed matching criteria.

7. A computer readable program on a tangible medium for comparing oscillations during a blood pressure determination, comprising:
   a routine for acquiring at a pressure increment a first oscillation having one or more oscillation characteristics;
   a routine for acquiring at the pressure increment a second oscillation having the one or more oscillation characteristics;
   a routine for acquiring a time interval between the first oscillation and the second oscillation via a heart monitor signal generated by an independent heart rate monitoring device;
   a routine for selecting a set of matching criteria based upon the heart monitor signal;
   a routine for determining whether the time interval is substantially an integer multiple of a reference time interval using the selected set of matching criteria; and
   a routine for determining whether the first oscillation and the second oscillation are substantially equivalent based upon the respective one or more oscillation characteristics and upon the selected set of matching criteria.

8. The computer readable program on a tangible medium as recited in claim 7, wherein the one or more oscillation characteristics comprise a peak amplitude.

9. The computer readable program on a tangible medium as recited in claim 7, wherein the independent heart rate monitoring device is at least one of an electrocardiograph, a photoplethysmograph, an accelerometer, an impedance plethysmograph, and an acoustic heart monitor.

10. The computer readable program on a tangible medium as recited in claim 7 wherein the heart monitor signal is an electrocardiogram.

11. The computer readable program on a tangible medium as recited in claim 7, wherein the heart monitor signal comprises at least one of a heart rate, a measure of heart rate variability, and an indicator of the presence of arrhythmias.

12. The computer readable program on a tangible medium as recited in claim 7, wherein selecting a set of matching criteria comprises selecting one of a set relaxed matching criteria and a set of unrelaxed matching criteria.

13. A non-invasive blood pressure monitor, comprising:
   means for acquiring a first and a second oscillation at a pressure increment;
   means for independently acquiring a time interval between the first and second oscillations;
   means for selecting a set of matching criteria;
   means for determining whether the time interval is substantially an integer multiple of a reference time interval using the selected set of matching criteria; and
   means for determining whether the first oscillation and the second oscillation are substantially equivalent based upon the selected set of matching criteria.

14. The non-invasive blood pressure monitor as recited in claim 13, wherein the means for selecting a set of matching criteria comprises means for selecting a set of matching criteria based upon analysis of an electrocardiogram signal.

15. A non-invasive blood pressure monitor, comprising:
   a pressure cuff configured to be pressurized by a source of pressurized air via an inflate valve and configured to be deflated via a deflate valve;
   a pressure transducer configured to determine the pressure within the pressure cuff and to generate a pressure signal;
   a heart monitoring device configured to generate a heart monitor signal; and
   a processing unit configured to receive the pressure signal and the heart monitor signal; to acquire two or more oscillations at a pressure increment from the pressure signal; to determine a time interval separating two oscillations from the heart monitor signal; to select a set of matching criteria based upon the heart monitor signal; to determine whether the time interval is substantially an integer multiple of a reference time interval using the selected set of matching criteria; and to determine whether the two oscillations are substantially equivalent based upon the selected set of matching criteria.

16. The non-invasive blood pressure monitor as recited in claim 15, wherein the heart monitoring device comprises one of an electrocardiograph, a photoplethysmograph, an accelerometer, an impedance plethysmograph, and an acoustic heart monitor.

17. The non-invasive blood pressure monitor as recited in claim 15, wherein the heart monitor signal comprises at least one of a heart rate, a measure of heartbeat variability, and an indicator of the presence of heart beat irregularities.

18. The non-invasive blood pressure monitor as recited in claim 15, wherein the heart monitor signal comprises an electrocardiogram.

19. The non-invasive blood pressure monitor as recited in claim 15, wherein the matching criteria comprise one of a set of unrelaxed matching criteria and a set of relaxed matching criteria.

20. The non-invasive blood pressure monitor as recited in claim 15, wherein the processing unit is configured to determine whether the two oscillations are substantially equivalent by comparing a peak amplitude of each of the two oscillations.

* * * * *